United States Patent [19]

Mizutani et al.

[11] Patent Number: 5,057,428
[45] Date of Patent: Oct. 15, 1991

[54] BIOREACTOR

[75] Inventors: Satoru Mizutani; Shoichi Matsuda; Ryoichi Kunitake, all of Tokyo, Japan

[73] Assignee: Kirin Beer Kabushiki Kaisha, Japan

[21] Appl. No.: 424,062

[22] Filed: Oct. 19, 1989

[30] Foreign Application Priority Data

Oct. 20, 1988 [JP] Japan ................................ 63-262912

[51] Int. Cl.[5] .......................... C12M 3/06; C12M 3/04
[52] U.S. Cl. .................................... 435/285; 435/284; 435/288; 435/311; 435/312; 435/313
[58] Field of Search ............................ 435/283–286, 435/288, 299, 311, 312, 313, 813; 210/321.64, 321.87–321.89, 150, 151

[56] References Cited

U.S. PATENT DOCUMENTS

| | | | |
|---|---|---|---|
| 4,537,860 | 8/1985 | Tolbert et al. | 435/311 |
| 4,720,462 | 1/1988 | Rosenson | 435/285 |
| 4,833,083 | 5/1989 | Saxena | 435/288 |

Primary Examiner—David L. Lacey
Assistant Examiner—William H. Beisner
Attorney, Agent, or Firm—Ladas & Parry

[57] ABSTRACT

A bioreactor comprises a cylindrical tank, a cylindrical mesh member arranged inside the tank concentrically therewith so that the mesh member separates an inner space of the tank into an outside space defined between an inner wall of the tank and the mesh member and an inside space, these spaces being packed with a culture medium or a carrier, respectively, a plurality of oxygen supplying pipes extending axially inside or outside the mesh member for supplying an oxygen to the culture medium, culture medium supplying assembly for supplying the culture medium in the tank, and a plurality of culture medium recovery pipes extending axially inside or outside the mesh member for recovering the culture medium after utilized. The culture medium supplying assembly comprises a plurality of nozzle members which are arranged in the outside space described above or inside the mesh member so that the culture medium supplied through the nozzle members can flow radially inwardly or radially outwardly. The structure of the mesh member or the axial lengths of the nozzle members may be changed so as to axially uniformly supply the culture medium in the tank.

22 Claims, 9 Drawing Sheets

BIOREACTOR

BACKGROUND OF THE INVENTION

This invention relates to a bioreactor for carrying out cultivation of cells of animals or plants.

Bioreactors for carrying out fermentation or cultivation of cells of animals or plants include a fluid bed type in which a carrier immobilizing cell, enzyme, yeast or microorganism (totally called biological catalyst hereinafter) is maintained in a floating condition and a static bed type in which a carrier stabilizing or immobilizing the biological catalyst fills in a tower or column. The static bed type bioreactor is further classified into a hollow fiber type in which hollow fiber is utilized as a carrier and a packed bed type in which a granular carrier such as foam glass, three-dimensional mesh-shape carrier such as ceramic porous body, honey-comb-shape carrier or multi-layered plate-like carrier is utilized as a carrier.

For example, as a packed bed type bioreactor, there is known a bioreactor in which the granular carrier stabilizing the biological catalyst fills in a cylindrical tank and culture medium is fed into the tank from the lower portion towards the upper portion of the tank. With the bioreactor of this type, the culture medium is likely extruded and the packed bed is composed of a moving phase in which the culture medium flows and a stationary phase (packed material phase) in which the culture medium does not flow at all.

With the bioreactor of the type described above, however, nutritional concentration and dissolved oxygen concentration are gradually reduced during the passing through from an inlet, through which the culture medium with dissolved oxygen is fed, to an outlet, through which a product or used culture medium is recovered, and in the meantime, waste materials reversely increases. For this reason, activity of the biological catalyst is lowered at the outlet of the bioreactor and, hence, the biological catalyst does not effectively fulfill the function and productivity of useful substance is reduced, which constitutes a significant problem.

In order to solve this problem, there has been provided a bioreactor of the type in which the height H of the cylindrical tank is made substantially equal to a distance from the culture medium inlet to a portion just before a portion at which the nutritional concentration and the dissolved oxygen concentration have become their critical values and the productivity of the useful substance have been extremely reduced and the diameter D of the tank is made large to ensure a sufficient inner volume thereof. However, there is a limit for making small the ratio H/D, thus being difficult to scale up the tank.

The biological catalyst likely adheres on the upper surface of the carrier and, hence, the adhesive density of the biological catalyst on the lower side of the carrier is small, which results in the lowering of the productive efficiency. This is also a problem for the bioreactor of the type described above.

In addition, in the conventional bioreactor, since the culture medium is likely extruded and the biological catalyst is poured into the culture medium with relatively high density when the biological catalyst is immobilized in the granular carrier, it is difficult to uniformly immobilize the biological catalyst to the whole carriers in the tank. Accordingly, the immobilization density of the biological catalyst is lowered at a portion near the upper end of the tank (i.e. the outlet side of the bioreactor) and, hence, the productivity of the useful substance for the bioreactor is lowered.

These problems described above have been also caused with a horizontal type bioreactor provided with a tank having an axis extending horizontally, as well as the static bed type bioreactor including the hollow fiber and packed bed type bioreactor.

SUMMARY OF THE INVENTION

An object of this invention is to substantially eliminate defects or drawbacks encountered to the prior art described above and to provide a bioreactor of packed bed type capable of reducing the distribution of the concentration in a movable phase of a bioreactor and achieving fermentation or cultivation with improved high density and productivity.

This and other objects can be achieved according to this invention, in one aspect, by providing a bioreactor comprising a cylindrical tank, a cylindrical mesh member arranged inside the tank concentrically therewith so that the mesh member separates an inner space of the tank into inside and on outside spaces, the outside space being packed with a culture medium and an inside space packed with a carrier, a plurality of oxygen supplying pipes extending axially inside the mesh member for supplying an oxygen to the culture medium, culture medium supplying means for supplying the culture medium in the tank so as to flow the culture medium radially inwardly inside the tank, and a plurality of culture medium recovery pipes extending axially inside the mesh member for recovering the culture medium after utilized.

In another aspect according to this invention, there is provided a bioreactor comprising a cylindrical tank, at least one cylindrical mesh member arranged inside the tank concentrically therewith so that the mesh member separates an inner space of the tank into inside and on outside spaces, the outside space being packed with a carrier and an inside space packed with a culture medium, and a plurality of oxygen supplying pipes extending axially outside the mesh member for supplying an oxygen to the culture medium, culture medium supplying means for supplying the culture medium in the tank so as to flow the culture medium radially outwardly inside the tank, and a plurality of culture medium recovery pipes extending axially outside the mesh member for recovering the culture medium after utilized.

In preferred embodiments, the tank is constructed to be rotatable by a driving mechanism.

The mesh members is secured at both ends to the flanged seal members closing both end openings of the tank and the mesh member has a structure formed so that mesh sizes are gradually increased from the culture medium entering end towards the other end thereof. The culture medium supplying means may comprise a plurality of nozzle members which are arranged outside the mesh member in the former aspect of this invention and inside the mesh member in the latter aspect thereof so as to supply the culture medium in the tank axially uniformly in a direction radially inwardly or outwardly. The mesh member has a mesh structure having a size capable of passing the culture medium together with a biological catalyst and the culture medium recovery pipe has a porous structure capable of passing the culture medium but not passing the biological catalyst.

According to this invention of the characters described above, the culture medium introduced into the tank of a bioreactor can be uniformly distributed in the axial direction of the tank. The oxygen can be fed into the culture medium effectively. The culture medium introduced into the tank is radially fed through the mesh member and contact to the carrier. The biological catalyst is buried in the carrier and only the culture medium is recovered after utilized.

DESCRIPTION OF THE PREFERRED EMBODIMENTS

Figure 1:
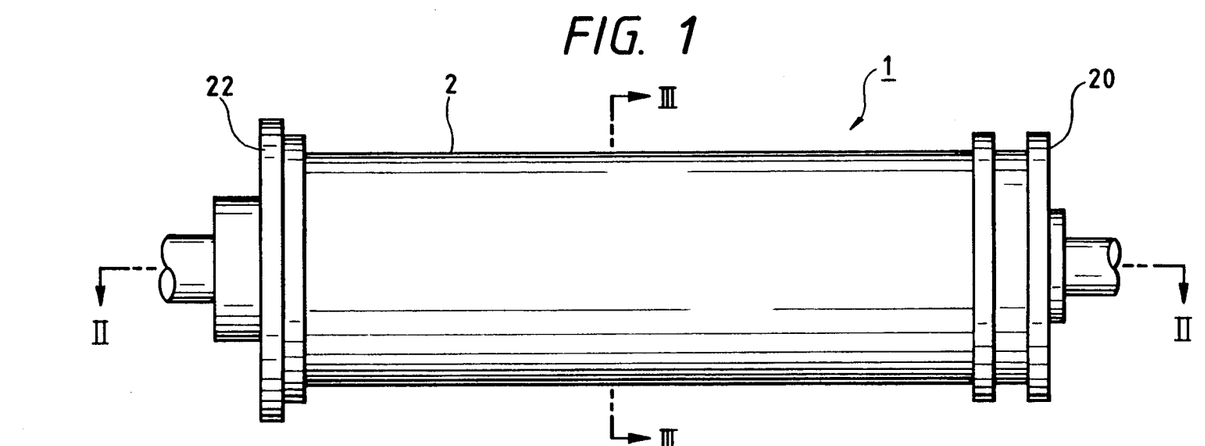
FIG. 1 is a side view of a bioreactor according to the first embodiment of this invention.
Figure 2:
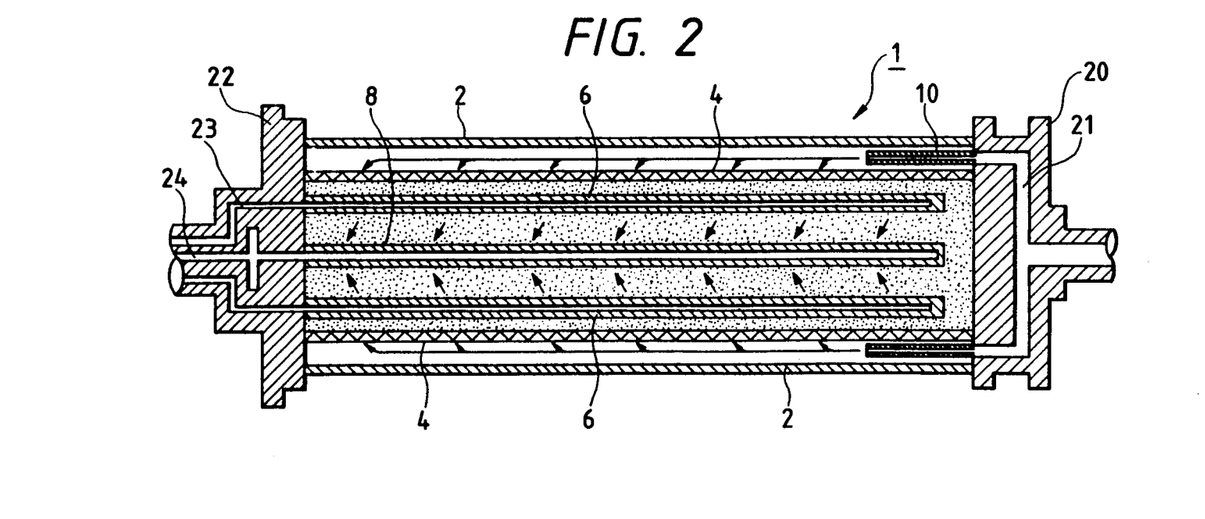
FIG. 2 is a longitudinal sectional view taken along the line II—II shown in FIG. 1.
Figure 3:
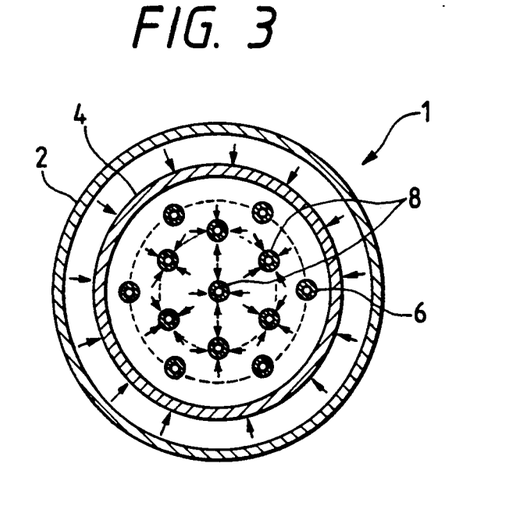
FIG. 3 is a cross sectional view taken along the line III—III shown in FIG. 1.

FIG. 1 shows a bioreactor according to this invention comprising a cylindrical tank 2 arranged horizontally. The cylindrical tank 2 is provided with both ends closed by flanged seal members 20 and 22. FIGS. 2 and 3 are sectional views taken along the lines II—II and III—III, respectively, shown in FIG. 1.

Referring to FIGS. 2 and 3, a cylindrical mesh member 4 is arranged concentrically with the cylindrical tank 2. A plurality of oxygen supplying pipes 6 and culture medium recovery pipes 8 are both concentrically arranged inside the mesh member 4 so as to axially extend in the tank 2. A carrier immobilizing enzyme and cell packs in the inside of the mesh member 4 in the tank 2. A plurality of nozzle members 10 through which culture medium is supplied are arranged in a space between the outer side of the mesh member 4 and the inner wall of the tank 2.

The tank 2 is made of a glass or metallic material which is usually utilized for the material of a bioreactor. The diameter and the axial length of the tank 2 can be optionally decided in accordance with a scale of the bioreactor. The flanged seal members 20 and 22 sealing both the ends of the tank body may be formed of the same material as that of the body of the tank 2. As shown in FIG. 2, a culture medium supply passage 21 for supplying the culture medium towards the culture medium supplying nozzle members 10 is formed in the flanged seal member 20. An oxygen supply passage 23 for supplying the to the oxygen supplying pipes 6 and a culture medium recovering passage 24 for feeding the culture medium, product and waste material recovered by means of the culture medium recovery pipes 8 to a system for the subsequent step are formed in the flanged seal member 22.

Figure 4:
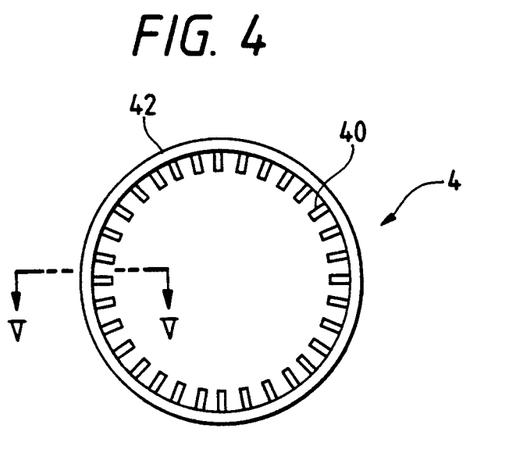
FIG. 4 is a view showing a wire mesh structure used for the first embodiment.
Figure 5:
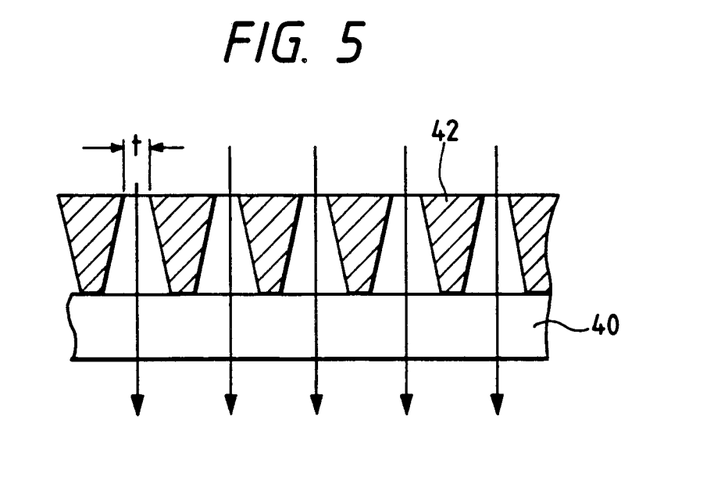
FIG. 5 is a sectional view taken along the line V—V shown in FIG. 4.

A typical example of the mesh member 4 will be represented, as shown in FIG. 4. A wire mesh which is formed by a wire 42 is wound around, in a spiral form with equal intervals, the outer surfaces of supporting rods 40 arranged on the same circumference with equal intervals. FIG. 5 is a sectional view taken along the line V-V shown in FIG. 4. Referring to FIG. 5, the dimension or size of the mesh member 4 is regulated by arranging the interval "t" between the adjacent spirals of the wire 42 to thereby determine the size of a particle which can pass the mesh member 4. The interval "t" is usually determined so as to have a range in which the biological catalyst together with the culture medium can pass the interval "t", whereas the carrier such as granular carrier cannot pass the interval "t". For example, in a case where granular carriers, the average diameter of which is about 1 mm, is utilized, it is desired to determine the interval "t" to a value about half (0.5 mm) of the diameter of each particle. Another type of mesh member such as punching metal in form of a metal net may be utilized in substitution for the wire mesh member. At any rate, the mesh member 4 is arranged in the tank 2 concentrically therewith and the both end openings of the mesh member 4 are closed by the flanged seal members 20 and 22 as shown in FIG. 2. According to the arrangement of the mesh member 4, the interior of the tank 2 is divided into inner and outer spaces and the inner space is packed with the carrier for immobilizing the biological catalyst. The diameter of the mesh member 4 will be optionally designed in consideration of the diameter of the tank 2 and the packing amount of the carrier.

Figure 6:
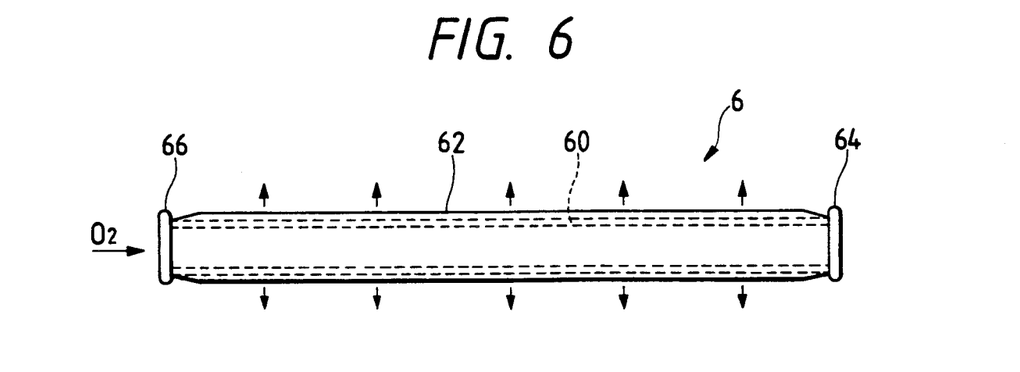
FIG. 6 is a side view showing a pipe structure used for this invention as an oxygen supplying pipe.

The oxygen supplying pipes 6 are arranged for the purpose of supplying the oxygen by the amount substantially corresponding to that consumed in the culture medium by the cells to keep constant the dissolved oxygen concentration The cells of animals or plants are not provided with cell membranes such as observed with the cells of microorganisms, so that the former cells are liably mechanically damaged and, in a certain case, the cells may be sheared by turbulent flow caused at vanishing time of bubbles of oxygen existing in the culture medium. Accordingly, it is desired to supply the oxygen into the culture medium through the oxygen supplying pipes 6 so as not to generate oxygen foam. FIG. 2 and FIG. 6 show the oxygen supplying pipes 6 each designed so as to attain the function described above. As shown in FIGS. 2 and 6, the oxygen supplying pipe 6 comprising a supporting pipe structure 60 made of a sintered porous SUS, stainless steel, having one opening end connected to the flanged seal member 22 so as to communicate with the passage 23 is formed therein. The outer peripheral surface of the pipe structure 60 is covered with a porous TEFLON, polytetrafluoroethylene, film 62 having a water repellency and both the ends of the pipe structure 60 are sealed with O-rings 64 and 66.

Figure 7:
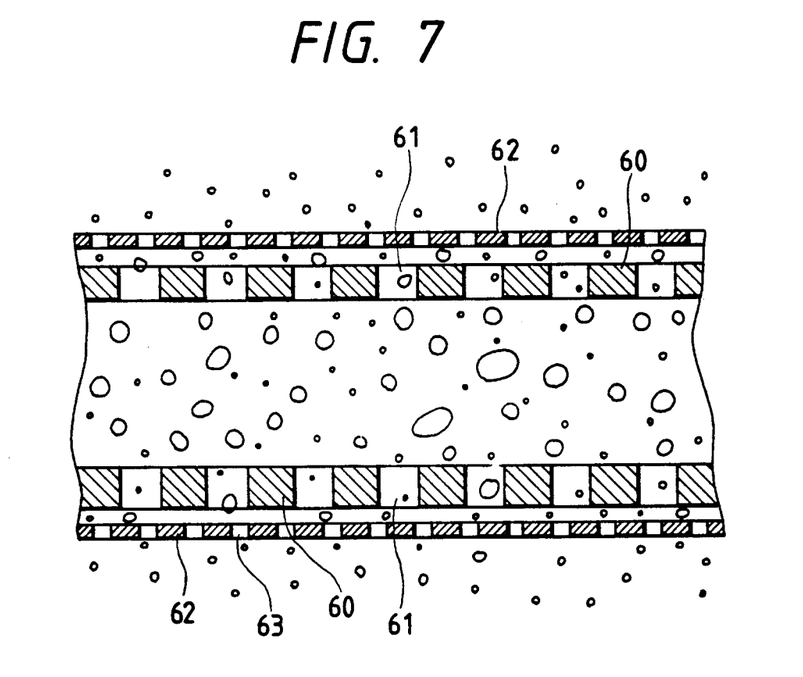
FIG. 7 is an enlarged sectional view of a part of the pipe structure shown in FIG. 6.

FIG. 7 is an enlarged sectional view of a part of the oxygen supplying pipe 6 shown in FIG. 6, in which the oxygen in the SUS, stainless steel, pipe structure 60 passes the pores 61 and then passes the pores 63 of the porous TEFLON, polytetrafluoroethylene, film 62 into the culture medium in the tank 2. Since the diameter of each of the pores 63 is usually of about 0.01 to 1.0 $\mu$m, the oxygen supplied into the culture medium through the pores 63 can be dissolved in the culture medium without generating any foam.

According to this invention, the porous TEFLON, polytetrafluoroethylene, film 62 may be substituted with a silicon thin film having a water repellency and when the silicon thin film is coated on the outer peripheral surface of the SUS, stainless steel, pipe structure 60, the oxygen passing the pores 61 then passes spaces between molecular branches of the silicon thin film and dissolved in the culture medium without generating any foam.

The oxygen to be supplied into the culture medium through the oxygen supplying pipe 6 may be substituted with an air.

The oxygen supplying pipes 6, six in the embodiment illustrated in FIG. 3, of the character described above are arranged at circumferential portions concentrically with the location of the mesh member 4 in the inside of the mesh member 4 with equal intervals. The arrangement and the number of the oxygen supplying pipes 6 may be optionally selected as occasion demands in accordance with the size or capacity of the bioreactor.

Figure 17:
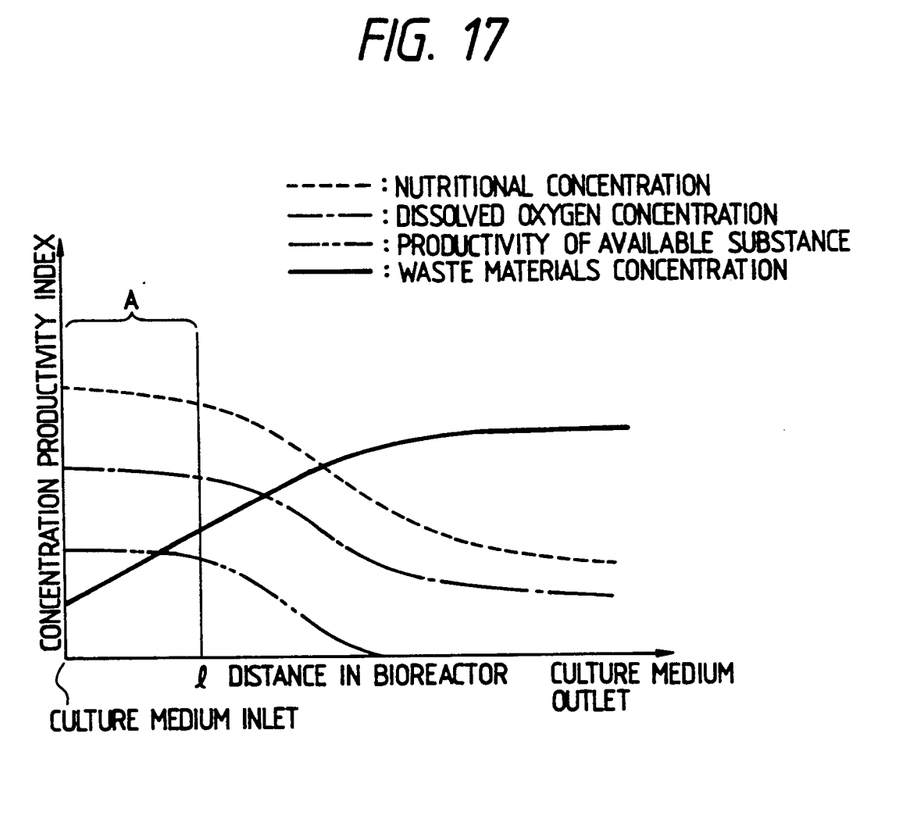
FIG. 17 is a view showing a relationship between a distance from the culture medium inlet to an outlet portion in the bioreactor and index of concentrations and productivity.

The culture medium recovery pipe 8 serves to recover products produced in the bioreactor, used culture medium and waste material and to feed them to the next system for carrying out purification, for example. The culture medium recovery pipe 8 comprises a pipe structure made of sintered porous SUS, stainless steel, and having one opened end which is connected to the flanged portion 22 so as to communicate with the passage 24 for recovering the culture medium as shown in FIG. 2. The recovery pipe 8 is disposed at a portion in the tank 2 apart from the mesh member 4 by a distance smaller than the distance described hereinbefore as shown in FIG. 17, i.e. the distance from the culture medium inlet just before a portion at which the nutritional concentration, the dissolved oxygen concentration and the available substance productivity are extremely lowered. Namely, the culture medium passing the mesh member 4 radially inward of the tank and passing the carrier immobilizing the biological catalyst can be recovered through the culture medium recovery pipe 8 without flowing over the distance 1. Accordingly, the contact distance between the culture medium and the static phase can be maintained substantially constant, whereby the nutritional concentration, the dissolved oxygen concentration and the available substance productivity can be maintained with high precision. The distance 1 may be optionally selected in accordance with the kinds or types of the biological catalyst to be utilized. The embodiment shown in FIG. 3 includes seven culture medium recovery pipes 8, six being arranged at circumferential portions concentrical with the inside mesh member 4 with equal intervals and the other one being arranged at substantially the central portion of the tank 2. The arrangement and the number of the recovery pipes 8 may be determined in accordance with the diameter of the mesh and the distance described above as occasion demands. Moreover, the diameter of each pore of the SUS, stainless steel, pipe structure of the recovery pipe 8 will be selected from a value ranging 1 to 50 $\mu$m, 20 $\mu$, for example, in which the culture medium can pass, but the biological catalyst cannot pass.

Figure 8:
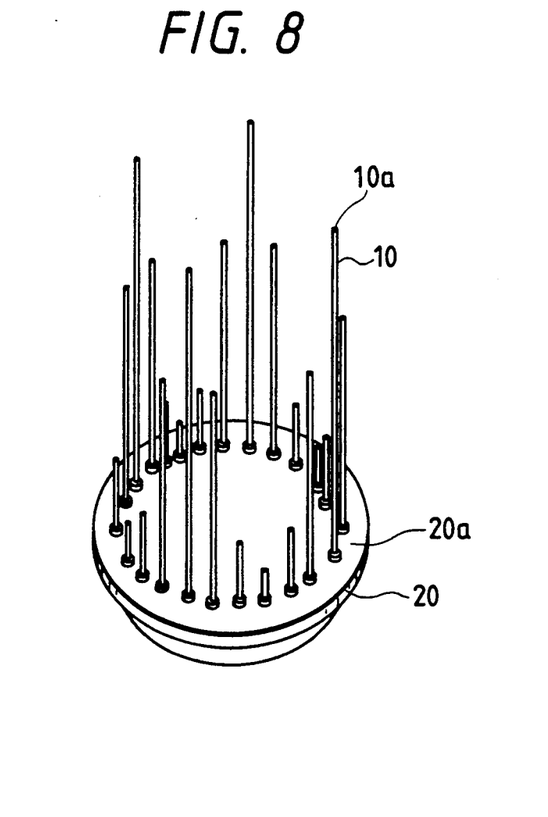
FIG. 8 is a perspective view of one example of arrangement of culture medium supplying nozzles utilized for this embodiment.

The culture medium supplying nozzle member 10 is arranged so as to axially extend in the tank 2 between the inner wall of the tank 2 and the mesh member 4 to supply the fresh culture medium axially uniformly in the tank 2. In the embodiment illustrated in FIG. 2, a plurality of nozzles 10 each in shape of an injection needle are arranged in the tank 2 in a manner that one opened ends thereof are connected to the flanged seal member 20 so as to communicate with the culture medium supply passage 21. In a typical embodiment, the culture medium supplying nozzles 10 are arranged at the circumferential portions with equal intervals concentrically with the tank 2 with axial lengths substantially equal to each other, but, in an alternation such as shown in FIG. 8, the axial lengths thereof may be periodically changed. Referring to FIG. 8, the flanged seal member 20 is provided with an inner surface 20a facing inside the tank 2 and a plurality of nozzles 10 for supplying the culture medium are arranged at circumferential portions of a circle coaxial with the outer circular edge of the surface 20a with substantially equal intervals so as to extend perpendicularly with respect to the surface 20a. The respective nozzles 10 are provided with front end openings 10a and the distances from the base ends of the respective nozzles to the front end openings 10a thereof, i.e. the axial lengths thereof, are periodically changed. For example, the lengths of the respective nozzles 10 may be selected so that a line connecting the front ends 10a of the respective nozzles 10 constitutes a sine curve or wave curve, for example, along the circumferential direction of the arrangement of the nozzles 10. The lengths and the numbers of the nozzles 10 may be determined optionally in accordance with the size or dimension of the bioreactor so that the front end portions 10a thereof are uniformly disposed in the axial and circumferential directions in the tank 2. Although, in the illustrated embodiment, the culture medium supplying nozzles 10 are arranged on the single circumference, but, in a modification, the nozzles may be arranged on a plurality of circumferences.

According to the location of the culture medium supplying nozzles 10 of the character described above, the culture medium is prevented from passing merely a portion near the flanged seal member 20 (culture medium supplying side), that is, so-called a short pass supply can be prohibited, whereby the culture medium can be axially uniformly supplied in the tank 2.

In a modification according to this invention, the culture medium supply nozzles 10 may be eliminated and, in this modification, in which a wire mesh is utilized, the wire mesh may have such arrangement as that intervals t, as shown in FIG. 5, of the adjacent wires constituting the wire mesh are changed in a gradually increasing manner from the flanged seal member 20 side towards the flanged seal member 22 side to increase the mesh size in this direction. Namely, by changing the intervals t in a range in which the carriers immobilizing the biological catalyst cannot pass the mesh in the above described manner, the culture medium can easily pass the mesh at a portion, having the large intervals "t", apart from the flanged seal member 20, i.e. the culture medium supplying side, whereby the culture medium will substantially uniformly pass the mesh in the axial direction thereof in the tank 2.

According to this invention, an adhesive animal cell such as CHO cell or BHK cell, yeast or microorganism, or the like may be utilized as the biological catalyst. A various kind of known carriers immobilizing the biological catalyst superior in the biological affinity may be utilized for the carrier in this invention and a granular carrier, or a three-dimensional net shaped carrier may be also utilized. The granular carrier includes a bead carrier, a particle carrier, a hollow spherical carrier and a, Raschig ring carrier, and the three-dimensional net shaped carrier includes a ceramic porous body, a foam polymer carrier, a fobered carrier, etc.

Figure 9:
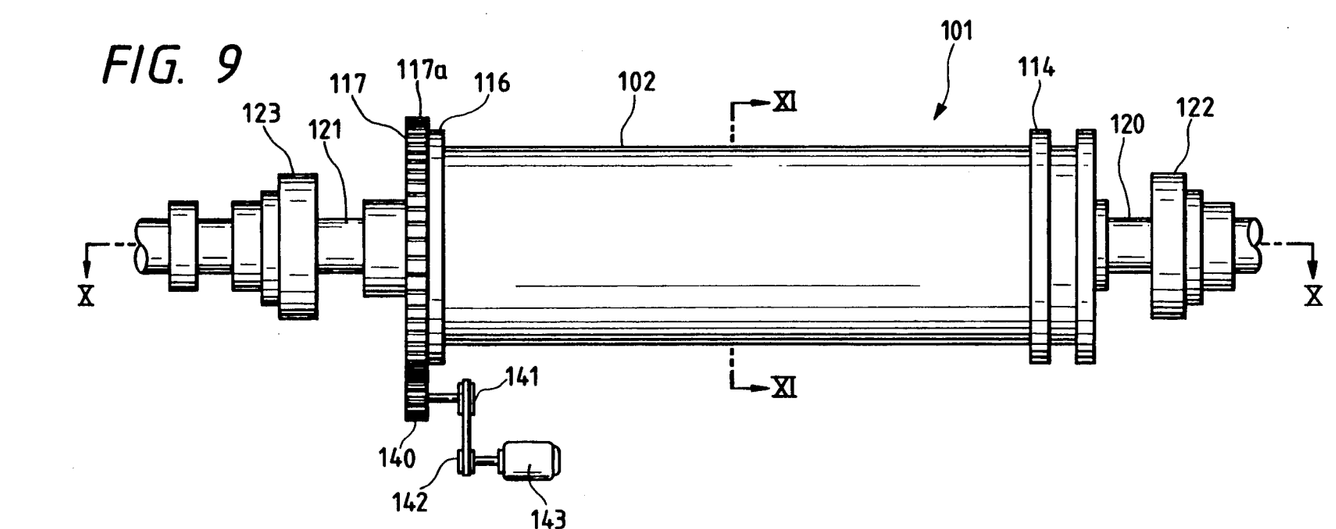
FIG. 9 is a side view of a bioreactor according to the second embodiment of this invention.

The bioreactor according to this invention may be constructed to be rotatable about the central axis thereof. FIG. 9 shows one embodiment of the rotary type bioreactor according to this invention. Referring to FIG. 9, the bioreactor 101 is provided with a cylindrical tank 102 with the axis extending horizontally and both ends of the tank 102 are closed by circular flanged seal members 114 and 116. The outer periphery of the flanged portion 117 of the flanged seal member 116 is formed so as to exhibit teeth shape so that the flanged portion 117 itself acts as a rotating gear 117a (spur gear) which is meshed with a drive gear 140 driven by a speed reduction motor 143 through power transmission members 141 and 142. Shaft members 120 and 121 are disposed in a projecting manner from the central portions of the outside surfaces of the flanged seal members 114 and 116. The shaft members 120 and 121 are supported by bearing members 122 and 123, respectively. According to this arrangement, when the drive gear 140 is rotated by the speed reduction motor, the gear 117a rotates about the central axis of the tank to thereby rotate the bioreactor 101.

Figure 10:
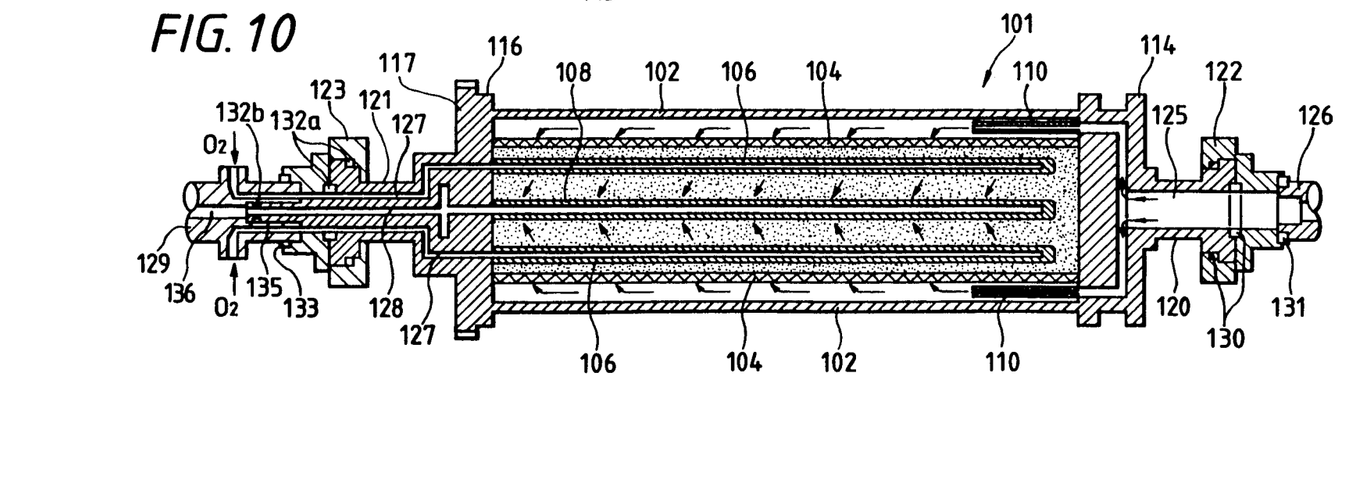
FIG. 10 is a longitudinal sectional view taken along the line X—X shown in FIG. 9.
Figure 11:
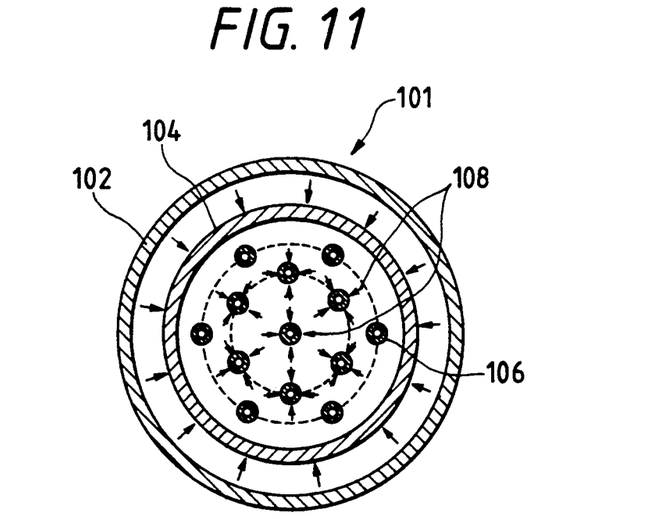
FIG. 11 is a cross sectional view taken along the line XI—XI shown in FIG. 9.

FIGS. 10 and 11 are sectional views taken along the lines X—X and XI—XI shown in FIG. 9 and referring to FIGS. 10 and 11, the inside structure of the tank 102 has substantially the same as that of the embodiment shown in FIG. 2. The cylindrical mesh member 104 is disposed in the tank 102 concentrically therewith and a plurality of oxygen supplying pipes 106 and a plurality of culture medium recovery pipes 108 are coaxially arranged inside the mesh member 104. The carrier for immobilizing the biological catalyst packs inside the mesh member 104. A plurality of culture medium supplying nozzle members 110 are arranged in a space between the inner wall of the tank 102 and the outer surface of the mesh member 104. The mesh member 104, the oxygen supplying pipes 106, the culture medium recovery pipes 108, and the culture medium supplying nozzle members 110 have substantially the same structures as those of the former embodiment, so that the details thereof are now eliminated herein.

As shown in FIG. 10, the shaft member 120 of the flanged seal member 114 is supported liquid-tightly by the bearing member 122 through a rotary seal 130 and a culture medium supplying pipe 126 is connected liquid-tightly to the bearing member 122 through a seal member 131 so as to communicate with a culture medium supply passage 125 which in turn communicates with the culture medium supplying nozzle members 110. The shaft member 121 of the flanged seal member 116 is supported air-tightly through a rotary seal 132a by the bearing member 123. A culture medium recovery pipe 129 is connected to the shaft member 121 air-tightly and liquid-tightly through a rotary seal 132b and a seal member 133 so that an oxygen supply passage 135 and a culture medium recovery passage 136 formed in the bearing member 123 communicate with the oxygen supply passage 127 and the culture medium recovery passage 128 formed in the shaft member 121. As described hereinbefore, when the drive gear 140 is driven by the speed reduction motor 143, the tank 102, the flanged seal member 114 (shaft member 120) and the flanged seal member 116 (shaft member 121) are integrally rotated.

The rotation of the bioreactor facilitates the adhesion of the biological catalyst uniformly and with high density throughout the whole surface area of the static bed and improves the function of the static bed. Moreover, the nutritional concentration and the dissolved oxygen concentration can be also uniformed, whereby the metabolic activity of the biological catalyst can be maintained and the productivity of the products by the bioreactor of this invention can be extremely improved.

The rotation speed of the bioreactor according to this invention can be optionally set to a suitable value by taking into consideration the kind or type of the biological catalyst to be used and the scale of the bioreactor to be used. For example, when animal cells are used, it is desired to rotate the bioreactor with the speed of revolution of about 0 to 16, preferably 0 to 3 revolutions/hour.

With the embodiment of this invention described above, the culture medium in the tank 2 or 102 flows radially inwardly from the outer side of the tank, but in a modification of this invention, it is possible to flow the culture medium radially outwardly from the inner side of the tank.

Figure 12:
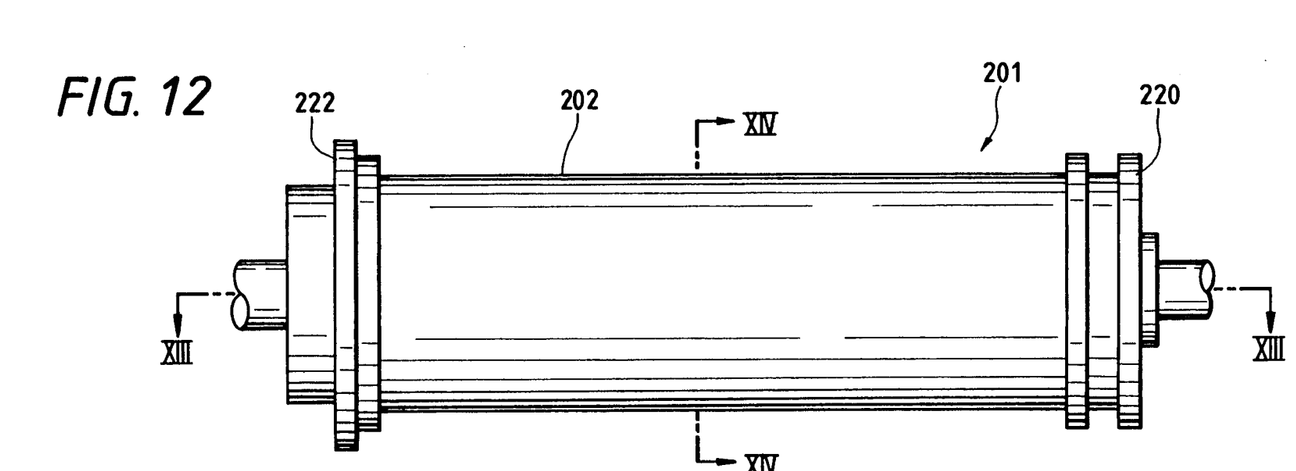
FIG. 12 is a side view of a bioreactor according to the third embodiment of this invention.
Figure 13:
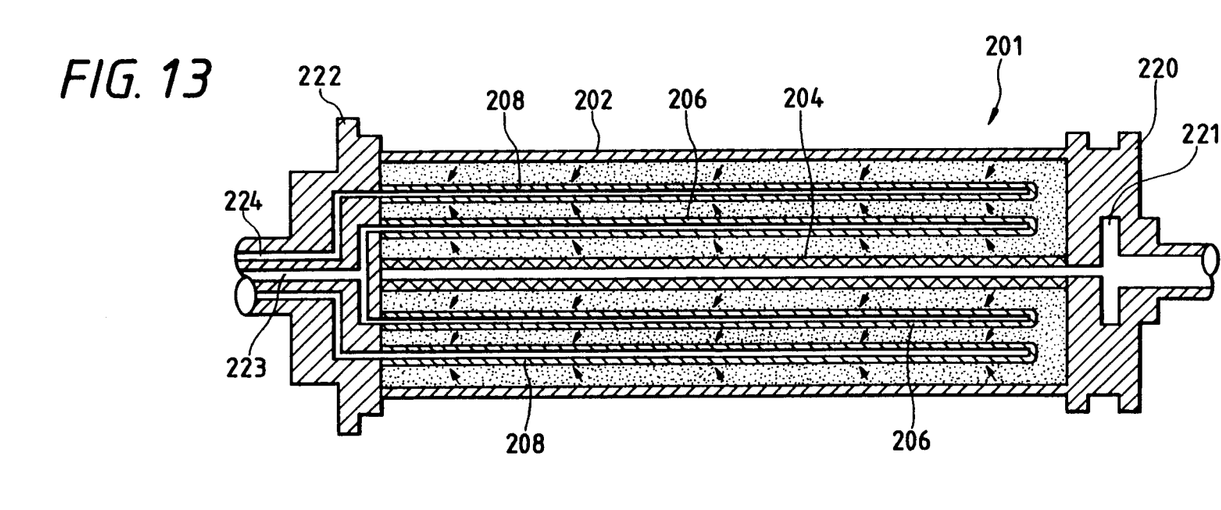
FIG. 13 is a longitudinal sectional view taken along the line XIII—XIII shown in FIG. 12.
Figure 14:
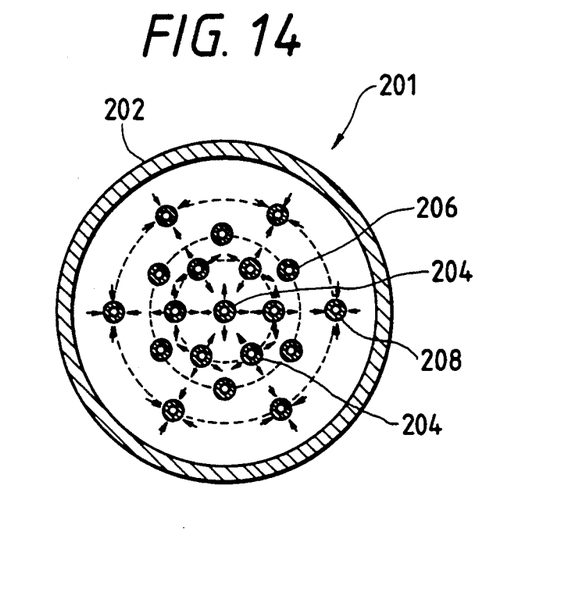
FIG. 14 is a cross sectional view taken along the line XIV—XIV shown in FIG. 12.

FIGS. 12 to 14 show a further embodiment of a bioreactor according to this invention, in which a plurality of cylindrical mesh members 204, a plurality of oxygen supplying pipes 206 and a plurality of culture medium recovery pipes 208 are arranged so as to axially extend in a tank 202.

Each of the cylindrical mesh members 204 has a diameter smaller than that of the mesh member 4 or 104 in the former embodiments. With the embodiment shown in FIG. 14, seven mesh members 204 are arranged, one being arranged at the central portion of the tank 202 and the other six being arranged at portions on the same circumference. Each of these meshes 204 communicates with a culture medium supplying passage 221 formed in a flanged seal member 22 and the structure of the mesh member 204 may accord with that shown in FIG. 4 or 5. In this case, it is desired that the interval t of the adjacent wires 42 constituting the mesh structure is gradually increased from the flanged seal member 220 side (culture medium supplying side) towards the flanged seal member 222 side. The culture medium can be pass uniformly throughout the axial direction of the mesh members 204 by changing the interval t in the manner described above. This interval t is set to a range, as described with reference to the former embodiments, in which the biological catalyst together with the culture medium ca pass the meshes, but the carrier cannot pass the same.

Figure 15:
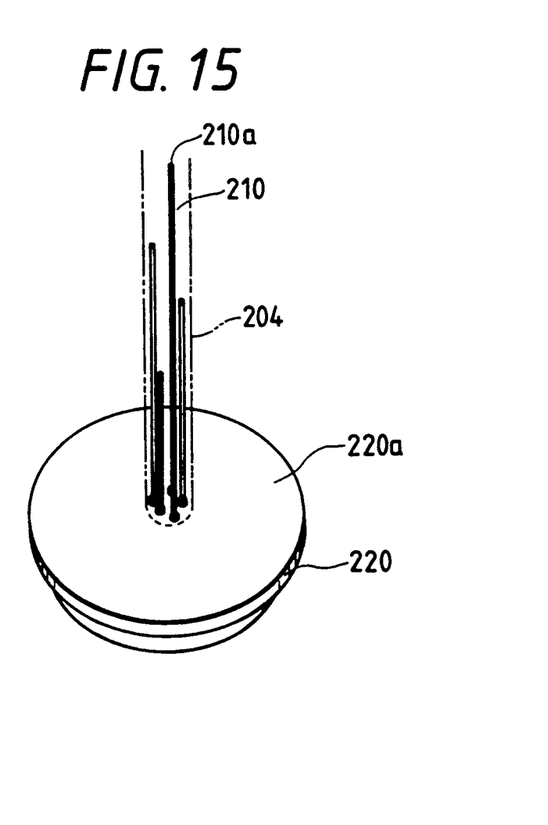
FIG. 15 is a perspective view of one example of arrangement of culture medium supplying nozzles utilized for this embodiment.

The culture medium supplying nozzles of the character described above may be arranged in the mesh members 204 having the constant wire interval t. Namely, as shown in FIG. 15, a plurality of culture medium supplying nozzle members 210 are arranged on the inner surface 220a of the flanged seal member 220 facing inside the tank 202 at portions on the circumference concentric with the circular outer periphery of the fanged seal member 220 so as to extend axially inward of the tank 202 and the mesh member 204 are disposed so as to surround the culture medium supplying nozzles 210. The culture medium can be uniformly supplied to the carrier by arranging the culture medium supplying nozzle members 21 so that the front ends 210a of the nozzles 210 may evenly exist in the meshes 204.

The oxygen supplying pipes 206 each has a structure substantially the same as that described with reference to the former embodiment and, accordingly, the opened end of the pipe 206 is connected to the flanged seal member 222 so as to communicate with the oxygen supply passage 223. The respective oxygen supplying pipes 206 are arranged at portions on the circumference concentric with the tank 202 outside the arrangement of the meshes 204.

The culture medium recovery pipes 208 each also has a structure substantially the same as that described with reference to the former embodiment and at least one culture medium recovery pipe 208 is arranged within a range apart from the meshes 204 by the distance l. In the embodiment illustrated in FIG. 14, the six culture medium recovery pipes 208 are arranged at portions on the circumference concentric with the tank 202. Each of pores of the porous sintered SUS, stainless steel, pipe structure constituting the culture medium recovery pipe 208 is formed so as to have a diameter so that the culture medium can pass the pores but the biological catalyst cannot pass the pores, i.e. to have a diameter of about 0.1 to 50 $\mu$m.

The carriers immobilizing the biological catalyst are packed inside the tank 202 and the culture medium is supplied through the culture medium supplying passage 221 to the respective mesh members 204 and finally flow out inside the tank 202. The culture medium supplied in the tank 202 moves in the tank 202 in the radial direction thereof while contacting the static phase and then recovered by the culture medium recovery pipes 208 together with the products and the effete or waste material.

The bioreactor of this embodiment may be also constructed to be rotatable as described with reference to the former embodiment.

Figure 16:
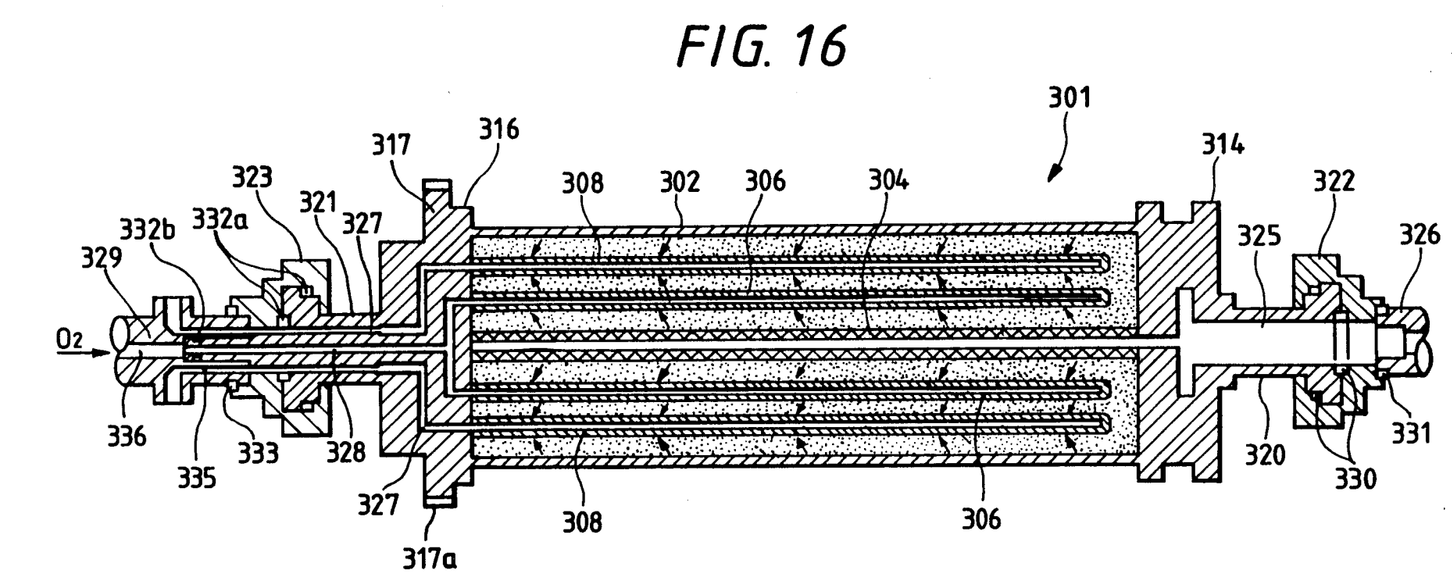
FIG. 16 is a longitudinal sectional view of the fourth embodiment according to this invention.

FIG. 16 shows a sectional view of a rotary type bioreactor according to this invention. Referring to FIG. 16, the tank 302 of the bioreactor 301 has substantially the same inner structure as that of the tank 202 shown in FIG. 13. A plurality of mesh members 304, a plurality of oxygen supplying pipes 306 and a plurality of culture medium recovery pipes 308 are arranged in the tank 302 so as to extend in the same axial direction therein and the carriers are packed in a space between the inner wall of the tank 302 and the mesh members 304. A flanged seal member 314 closing one end, i.e. culture medium supplying side, of the tank 302 has a shaft portion 320 which is supported liquid-tightly by a bearing member 322 through a rotary seal 330. A culture medium supplying pipe 326 is connected liquid-tightly to the bearing member 322 through a seal member 331 so as to communicate with a culture medium supplying passage 325 formed in the shaft 320. A flanged seal member 316 closing the other one end, i.e. culture medium recovery side, of the tank 302 has a shaft portion 321 which is supported air-tightly by a bearing member 323 through a rotary seal 332a. A culture medium recovery pipe 329 is connected to the bearing member 323 air-tightly and liquid-tightly through a rotary seal 332b and a seal member 333 so as to communicate with an oxygen supplying passage 328 and a culture medium recovery passage 327 both formed in the shaft 321.

Both the flanged seal members 314 and 316, i.e. shafts 320 and 321 are integrally rotated by driving a speed reduction motor, not shown in the manner described with reference to the former embodiment through a drive gear meshing with a gear 317a formed on the outer periphery of the flanged portion 317 of the flanged seal member 316. The speed of rotation of the bioreactor 301 may be optionally determined to a suitable condition in accordance with the kinds or types of the biological catalyst to be used or the size or scale of the bioreactor to be utilized and, for example, when the animal cells are used, it is desired to determine the revolution speed to about 0 to 16, preferably 0 to 3, revolutions/hour.

With this embodiment, the arrangement of the culture medium supplying nozzle members 210 (FIG. 15) is substantially the same as that of the embodiment shown in FIG. 15.

With this embodiment, as described before, a granular carrier, a three-dimensional net shaped carrier, a honey-comb shaped carrier, a multi-layered plate-like carrier, or a hollow fiber type carrier may be utilized as a carrier.

In the bioreactors of the embodiments described above, the biological catalyst is uniformly immobilized in the carrier in the following manner. The culture medium including the biological catalyst supplied in the tank of the bioreactor flows axially entirely in the inside of the tank and passes radially through the mesh or meshes together with the biological catalyst and further radially flows while contacting the carrier. During this flow, the biological catalyst in the culture medium is uniformly immobilized in the carrier and, accordingly, only the culture medium is recovered by the culture medium recovery pipe.

It is to be understood by persons skilled in the art that this invention is not limited to the embodiments described hereinbefore and many changes and modifications may be made without departing from the spirit and scope of the appended claims.

What is claimed is:

1. A bioreactor comprising:
   a cylindrical tank;
   a cylindrical mesh means arranged inside said tank concentrically therewith so that said cylindrical mesh means separates an inner space of said tank into inside and outside spaces, said outside space being filled with a culture medium including a biological catalyst and said inside space packed with a carrier;
   an oxygen supplying means comprising a plurality of pipes each having pores through which oxygen is supplied in the culture medium and extending axially in said inside space for supplying an oxygen to the culture medium;
   means for supplying the culture medium in said outside space so as to flow the culture medium radially inwardly inside the tank; and a culture medium recovery means comprising a plurality of pipes extending axially in said inside space for recovering the culture medium after utilized, said mesh means having a mesh structure having a mesh size larger than a size of the biological catalyst and said culture medium recovery pipes each having a porous structure provided with pores each having a pore size smaller than the size of the biological catalyst.

2. A bioreactor according to claim 1, further comprising a driving mechanism for rotating said tank about a central axis thereof.

3. A bioreactor according to claim 1, wherein said plurality of oxygen supplying pipes are disposed with substantially equal spaces in a circumferential arrangement and said plurality of culture medium recovery pipes are disposed with substantially equal spaces in a circumferential arrangement, said circumferential arrangement of oxygen supplying pipes and said circumferential arrangement of culture medium recovery pipes being concentric with said tank.

4. A bioreactor according to claim 3, wherein each of the oxygen supplying pipes comprises a sintered porous stainless steel pipe body and a porous polytetrafluoroethylene film formed on an outer peripheral surface of said sintered porous stainless steel pipe.

5. A bioreactor according to claim 3, wherein each of the oxygen supplying pipes comprises a sintered porous stainless steel pipe body and a silicon thin film coating an outer peripheral surface of said sintered porous stainless steel pipe.

6. A bioreactor according to claim 1, wherein said tank is provided with open longitudinal end portions, said open end portions being closed by seal members, respectively.

7. A bioreactor according to claim 6, wherein the mesh means is secured at both ends to said seal members and wherein each of the oxygen supplying and the culture medium recovery pipes is provided with one open end which is connected to a surface of one of said seal members, said surface facing the interior of the tank, said one of said seal members being provided with an oxygen supply passage and a culture medium recovery passage formed in said one of said seal members so as to communicate with said opened ends of said oxygen supplying pipes and said culture medium recovery pipes, respectively.

8. A bioreactor according to claim 7, wherein said mesh means has a structure such that its mesh sizes are gradually increased from a culture entering one end towards the other end secured to said one of side seal members.

9. A bioreactor according to claim 7, wherein the culture medium supplying means comprises a plurality of nozzle members secured at one end to an inner surface of the other one of said seal members so as to extend axially in said outside space, said other one of said seal members being provided with a culture medium supply passage formed therein so as to communicate with an open end of each of said nozzle members which is secured to the inner surface of the other one of said seal members.

10. A bioreactor according to claim 9, wherein said culture medium supplying nozzle members have a circumferential arrangement in which said nozzle members are disposed with substantially equal spaces in a circumferential direction, said circumferential arrangement being concentric with said tank.

11. A bioreactor according to claim 9, wherein said culture medium supplying nozzle members have axial length periodically different from each other.

12. A bioreactor comprising:
a cylindrical tank;
a mesh means comprising at least one cylindrical mesh member arranged inside said tank concentrically therewith so that said cylindrical mesh means separates an inner space of said tank into inside and outside spaces, said outside space being packed with a carried and said inside space filled with a culture medium including a biological catalyst;
an oxygen supplying means comprising a plurality of pipes each having pores through which oxygen is supplied in the culture medium and extending axially in said outside space;
means for supplying the culture medium in said inside space so as to flow the culture medium radially outwardly in the tank; and
a culture medium recovery means comprising a plurality of pipes extending axially in said outside space for recovering the culture medium after utilized, said mesh means having a mesh structure having a mesh size larger than a size of the biological catalyst and said culture medium recovery pipes each having a porous structure provided with pores each having a pore size smaller than the size of the biological catalyst.

13. A bioreactor according to claim 12, further comprising a driving mechanism for rotating said tank about a central axis thereof.

14. A bioreactor according to claim 12, wherein said plurality of oxygen supplying pipes are disposed with substantially equal spaces in a circumferential arrangement and said plurality of culture medium recovery pipes are disposed with substantially equal spaces in a circumferential arrangement, said circumferential arrangement of oxygen supplying pipes and said circumferential arrangement of culture medium recovery pipes being concentric with said tank.

15. A bioreactor according to claim 14, wherein each of the oxygen supplying pipes comprises a sintered porous stainless steel pipe body and a porous tetrafluoroethylene film formed on an outer peripheral surface of said sintered porous stainless steel pipe.

16. A bioreactor according to claim 14, wherein each of the oxygen supplying pipes comprises a sintered porous stainless steel pipe body and a silicon thin film coating an outer peripheral surface of said sintered porous stainless steel pipe.

17. A bioreactor according to claim 12, wherein said tank is provided with open longitudinal end portions, said open end portions being closed by seal members, respectively.

18. A bioreactor according to claim 17, wherein the mesh means is secured at both ends to said seal members and wherein each of the oxygen supplying and the culture medium recovery pipes is provided with one open end which is connected to a surface of one of said seal members, said surface facing the interior of the tanks, said one of said seal members being provided with an oxygen supply passage and a culture medium recovery passage formed in said one of said seal members so as to communicate with said opened ends of said oxygen supplying pipes and said culture medium recovery pipes, respectively.

19. A bioreactor according to claim 18, wherein one end of the mesh means secured to the other one of said seal members which is provided with a culture medium supply passage formed therein so as to communicate with an inner space of said mesh means through the one end thereof.

20. A bioreactor according to claim 42, wherein said mesh means has a structure such that its mesh sizes are gradually increased from the culture entering one end towards the other end secured to said one of said seal members.

21. A bioreactor according to claim 19, wherein said culture medium supplying means comprises a plurality of culture medium supplying nozzle members having one end secured to said other one of seal members so as to communicate with said culture medium supply passage formed in the seal member and having a circumferential arrangement in which said nozzle members are disposed with a substantially equal space in a circumferential direction, said arrangement and mesh means being concentric with said tank.

22. A bioreactor according to claim 21, wherein said culture medium supplying nozzle members have axial lengths periodically different from each other.

* * * * *